United States Patent
Kropfgans et al.

(10) Patent No.: US 6,242,628 B1
(45) Date of Patent: Jun. 5, 2001

(54) PROCESS FOR PREPARING ALKOXYSILANES

(75) Inventors: Frank Kropfgans; Hartwig Rauleder; Reinhold Schork, all of Rheinfelden (DE)

(73) Assignee: Degussa-Huels Aktiengesellschaft, Frankfurt (DE)

( * ) Notice: Subject to any disclaimer, the term of this patent is extended or adjusted under 35 U.S.C. 154(b) by 0 days.

(21) Appl. No.: 09/435,468

(22) Filed: Nov. 8, 1999

(30) Foreign Application Priority Data

Nov. 6, 1998 (DE) .............................................. 198 51 148
Aug. 31, 1999 (DE) .............................................. 199 41 590

(51) Int. Cl.[7] ..................................................... C07F 7/18
(52) U.S. Cl. ........................................... 556/471; 556/470
(58) Field of Search ..................................... 556/470, 471

(56) References Cited

U.S. PATENT DOCUMENTS

| | | | |
|---|---|---|---|
| 4,211,717 | * 7/1980 | Emblem et al. | ...................... 556/470 |
| 4,827,008 | * 5/1989 | Gousetis et al. | ...................... 556/471 |
| 5,616,755 | 4/1997 | Seiler et al. . | |
| 5,698,726 | 12/1997 | Rauleder et al. . | |

* cited by examiner

*Primary Examiner*—Paul F. Shaver
(74) *Attorney, Agent, or Firm*—Oblon, Spivak, McClelland, Maier & Neustadt, P.C.

(57) ABSTRACT

Alkoxysilanes are prepared by a process, comprising:

(i) reacting a chlorosilane with an alcohol in a water-free and solvent free phase with removal of the liberated hydrogen chloride;

(ii) transferring the resultant product mixture into a liquid phase to be distilled and adding a metal alcoholate to the product mixture in the liquid at a temperature in the range from 10–60° C., and thoroughly mixing the neutralized product mixture, said alcoholate being employed in an equimolar amount or in a stoichiometric excess based on the amount of acidic chloride, and (iii) purifying the treated product mixture by distillation under reduced pressure, thereby preparing alkoxysilanes which are low in acidic chloride or essentially free of acidic chloride.

18 Claims, No Drawings

PROCESS FOR PREPARING ALKOXYSILANES

BACKGROUND OF THE INVENTION

1. Field of the Invention

The present invention relates to a process for preparing alkoxysilanes which are low in acidic chloride or essentially free from acidic chloride.

2. Description of the Background

It is known that alkoxysilanes can be prepared by reacting the corresponding chlorosilanes with an alcohol as described in, for example, DE 28 00 017 C2 or EP 0 107 765 P2.

A concern in the course of such procedures is generally to maximize esterification and obtain a good product yield. The survival of unreacted fractions of chlorosilane and hydrogen chloride as what is known as hydrolyzable or acidic chlorine compounds, i.e., acidic chloride for short, in the product is not wanted. Within the group of organoalkoxysilanes, it is generally only the aminoalkylalkoxysilanes that include not only acidic chloride but also residues of nonhydrolyzable chlorine compounds such as chloroalkylalkoxysilane, since such compounds are starting compounds in the preparation of the aminoalkylalkoxysilanes; cf. EP 0 741 137 A1. For the present invention, aminoalkylalkoxysilanes are excluded from the group of alkoxysilanes.

In the light of the present-day uses of the alkoxysilanes such as, for example, as adhesion promoters, for the hydrophobicization of building protection products, for crosslinking plastics, for modifying surfaces, in glass fiber sizes, for example, and as starting materials for further reaction stages, to name but a few utility areas, therefore, it is necessary to provide products having a very low content of acidic chloride.

In the text which follows any reference to a chloride-free alkoxysilane is to a product whose acidic chloride content is less than 10 ppm by weight, i.e., which is essentially free from acidic chloride. The detection limit for determining acidic chloride in alkoxysilanes is currently <1 ppm by weight (as determined by argentometric titration in anhydrous acidic solution with potentiometric endpoint determination—AN-SAA-041 1).

EP 0 223 210 A2 discloses a method of purifying alkoxysilanes comprising hydrolyzable and nonhydrolyzable chlorine compounds, in which the alkoxysilane is heated in the presence of acid clay or a heavy metal halide, then brought into contact with a neutralizing agent such as metallic sodium, metallic calcium, alkali metal hydroxide, sodium carbonate, magnesium oxide, alkali metal alcoholate, ammonia, an organic amine, alkylene oxide or an ortho ester, and separated from the other components by means, for example, of filtration or distillation. In addition the filter residues arising from this method must be washed with solvent, in a laborious procedure, to remove all silane before they can be disposed of as special waste, or must be worked up and recycled, in a likewise laborious and costly procedure. The heating of said alkoxysilanes in the presence of acid clay or a heavy metal halide is also laborious and can result in unwanted secondary reactions. It is known, for instance, that when chloroalkylalkoxysilanes are heated in the presence of a metal halide such as iron chloride, aluminum chloride or copper chloride, to name but a few, they are broken down in a process which is accompanied by the liberation of HCl and the formation of alkenylalkoxysilanes. Product discoloration, the formation of mixed esters, and condensation reactions are also observed. Furthermore, because of the presence of traces of the heavy metal halide that is employed, alkoxysilanes obtained by such a method do not in general meet the stringent requirements of the food industry with respect, for example, to plastic packaging or pipes for drinking-water.

DE 25 21 399 discloses a process for preparing aminoalkylsilanes in which a reaction mixture obtained by aminating a chloroalkylalkoxysilane is admixed prior to workup with an amount of metal alcoholate equivalent to the amount of chloroalkylsilane and/or chloride present in the mixture. This preparation process makes use of solvents or diluents, such as toluene, hexane or alcohol.

EP 0 282 846 A2 discloses a process for preparing alkoxysilanes with a low content of chlorine compounds by stepwise esterification of chlorosilanes with alcohols in the liquid phase, with removal of the resulting hydrogen chloride. The alkoxysilanes obtained in this way, which still contain a small amount of chlorine compounds, are reacted with metal alcoholate, which, based on the amount of chlorine compounds, is added in a stoichiometric excess at a temperature in the range from 80–200° C. in the presence or absence of a solvent such as toluene or xylene, and the alkoxysilane is separated by filtration, for example, from the salts that have been formed. With this process, the long reaction times at relatively high operating temperatures are not very advantageous.

In addition, EP 0 486 279 B1 discloses a process comparable to the abovementioned processes which is intended to remove acidic impurities from alkoxysilanes and which uses, as a neutralizing agent, the metal salt of a sterically hindered amine or an alkali metal alcoholate of a sterically hindered alcohol at a temperature of up to 80° C. over 1–2 hours, the neutralized alkoxysilane being distilled. Neutralizing agents of this kind are not available in sufficient quantities for industrial scale operations and the separate additional preparation of the neutralizing agent would be complex, costly and therefore ruled out on economic grounds.

EP 0 532 872 B1 likewise discloses a process for preparing alkoxysilanes that are contaminated with hydrolyzable chlorine atoms, where the alkoxysilanes are reacted with an alcohol in a pressure reactor in the presence or absence of excess amounts of a neutralizing agent, reaction taking place at above the boiling point of the alcohol used and under the autogenous pressure, and the salt produced, if appropriate, is separated and the excess alcohol is removed from the product by distillation. Neutralizing agents disclosed in this case include ammonia, organic amines and sodium alcoholates. It is known that under the abovementioned conditions chloroalkylalkoxysilanes, in particular, are able to react with ammonia or with organic amines to form aminoalkylalkoxysilanes or, in the presence of alcohols and with alcoholates, to form alkyloxyalkylalkoxysilanes.

EP 0 563 883 B1 discloses a process for neutralizing acidic halides in alkoxysilanes which provides for the alkoxysilane to be brought into contact first with a metal alcoholate as a base, which, based on the content of the acidic halide, is added in a stoichiometric excess, and subsequently with an acidic salt which, based on the proportion of the residual base present in excess in the alkoxysilane, is employed in a stoichiometric excess. Here too, the salts are separated by filtration from the product, which can if desired be purified further by evaporating residual alcohol or by distillation. In addition, EP 0 563 883 B1 refers to problems in terms of the color quality of alkoxysilanes, these problems being observed during the workup, in particular during the neutralization and subsequent workup of the alkoxysilanes.

SUMMARY OF THE INVENTION

Accordingly, one object of the present invention is to provide a process which enables low-chloride or essentially chloride-free alkoxysilanes to be prepared simply and economically.

Briefly, this object and other objects of the present invention as hereinafter will become more readily apparent can be attained in a process of producing alkoxysilanes by (i) reacting a chlorosilane with an alcohol in a water-free and solvent free phase with removal of the liberated hydrogen chloride, (ii) transferring the resultant product mixture into a liquid phase to be distilled and adding a metal alcoholate to the product mixture in the liquid at a temperature in the range from 10–60° C., and thoroughly mixing the neutralized product mixture, the alcoholate being employed in an equimolar amount or in a stoichiometric excess based on the amount of acidic chloride, and (iii) distilling the treated product mixture under reduced pressure, thereby preparing purified alkoxysilanes which are low in acidic chloride or are essentially free of acidic chloride.

DETAILED DESCRIPTION OF THE PREFERRED EMBODIMENTS

A particular objective of the present invention is to provide a process, in particular, for the preparation of alkoxysilanes which carry a so-called nonhydrolyzable halogen in their functional groups, examples being 3-chloropropyltrialkoxysilanes, or else alkoxysilanes which are free per se from nonhydrolyzable halogen compounds such as tetraethoxysilane, alkyltrialkoxy-, dialkyldialkoxy- and alkylmethyldialkoxysilanes in which the linear, branched or cyclic alkyl groups contain preferably 1–20 carbon atoms, and for vinyltrialkoxysilanes, aryltrialkoxysilanes and arylalkyldialkoxysilanes, to name but a few.

It has been found that alkoxysilanes which are outstandingly low in acidic chloride or substantially free from acidic chloride can be prepared simply and economically by reacting a chlorosilane with an alcohol in a water-free and solvent-free phase and removing the liberated hydrogen chloride, preferably under reduced pressure and with thorough mixing, transferring the resultant product mixture into a liquid phase for subsequent distillation and adding a metal alcoholate at a temperature of from 10–60° C. to the product mixture in the liquid to neutralize acidic chloride compounds present, the alcoholate being employed in equimolar amounts or with a stoichiometric excess based on the content of acidic chloride in the product mixture, thoroughly mixing the base-comprising product mixture at the abovementioned temperature and subsequently purifying the product by distillation under reduced pressure. Advantageously, the neutralization products of base and acidic chloride can be discharged from the distillation unit together with the distillate residue. The process of the invention can be operated batchwise, but is preferably conducted as a continuous operation. A further ecological and economic advantage of the process of the invention is the solventless operation. It is noted that for the present process the alcohols are not counted as solvents. Furthermore, the present process is suitably operated in a liquid phase under an inert gas, preferably using nitrogen as the inert gas. The present process is generally operated under pressures which, suitably, are within the range from 0.1–1.5 bar abs.

Products prepared by the process of the present are prepared in very good yields and with an acidic chloride content of less than 5 ppm by weight; in fact, down to the analytical detection limit for acidic chloride. Furthermore, the process of the invention provides products notable for their very good color quality and excellent purity.

In the present process the alkoxysilane can be prepared by reacting a chlorosilane such as 2-chloroethyltrichlorosilane, vinylmethyldichlorosilane, allyltrichlorosilane, 3-allyloxypropyltrichlorosilane, butyltrichlorosilane, pentyltrichlorosilane, cyclopentyltrichlorosilane, cyclopentylmethyldichlorosilane, phenyltrichlorosilane, cyclohexyltrichlorosilane, octyl methyldichlorosilane, dodecyltrichlorosilane, benzyltrichlorosilane, benzylmethyldichlorosilane, 2-phenylethyltrichlorosilane or diphenyldichlorosilane or, preferably, tetrachlorosilane, methyltrichlorosilane, dimethyldichlorosilane, trimethylchlorosilane, ethyltrichlorosilane, 3-chloropropyltrichlorosilane, 3-chloropropylmethyldichlorosilane, cyclohexylmethyldichlorosilane, vinyltrichlorosilane, propyltrichlorosilane, propylmethyldichlorosilane, isobutyltrichlorosilane, amyltrichlorosilane, octyltrichlorosilane, hexadecyltrichlorosilane and hexadecylmethyldichlorosilane, with, for example, a monohydric primary alcohol having 1–20 carbon atoms such as methanol, ethanol, propanol or butanol, or, if desired, with a branched alcohol having 1–20 carbon atoms such as isopropanol, sec-butanol, tert-butanol or amyl alcohol, or with a cyclic alcohol, such as cyclopentanol or cyclohexyl alcohol, or with an aromatic alcohol such as benzyl alcohol, 2-phenylethanol, cinnamyl alcohol or di- or triphenylmethanol, or with a monoether of a polyalkylene glycol such as methyl, ethyl, propyl or butyl glycol, or with a di-, tri- or tetramethylene glycol monomethyl, monoethyl, monopropyl or monobutyl ether, or with a dihydric aliphatic alcohol such as ethylene glycol, 1,2-propylene glycol or 1,2-butylene glycol, or with a diol having 3–12 carbon atoms, where the carbon chain can be straight or branched, to name but a few alcohols, with liberation of hydrogen chloride.

In general the reaction takes place under reflux conditions. Alternatively, the esterification can be conducted at a lower temperature, under reduced pressure if desired; for example, in the range from 50–70° C. and over a period from 5–24 hours. In some cases, as with haloorganoalkoxysilanes, for example, esterification is more difficult. Nevertheless, the process of the invention is an economic procedure which is very gentle to the product.

In order to remove the hydrogen chloride, which results from the reaction of chlorosilane and alcohol, preferably alcohol is added in liquid form continuously and at the same time an unreacted fraction of the alcohol employed is drawn off from the top of the distillation unit as a gas phase, so that the alcohol employed additionally serves to strip HCl from the unit. In this case it is also possible to operate under reduced pressure. By means of this comparatively simple but, in the case of the present process, highly effective procedure of HCl removal, it is possible in the present process to achieve virtually complete esterification and so, advantageously, to raise the conversion rates to levels of up to 99.9%.

The alcohol employed in the process of the invention is, in particular, methanol, ethanol, n-propanol, isopropanol, methylglycol, ethylglycol or a mixture of two or more of the abovementioned alcohols.

Preferred alkoxysilanes of the invention have formula I or II below:

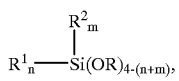  (I)

where
  R is a linear or branched $C_{1-4}$-alkyl or a glycol ether unit of the formula: —[(CH$_2$)$_y$—O]$_z$—R$^3$ in which y is 2, 4, 6 or 8, z is 1, 2, 3 or 4 and R$^3$ is a linear or branched $C_{1-8}$-alkyl group,
  R$^1$ is a linear, branched or cyclic $C_{1-20}$-alkyl group, a linear, branched or cyclic chloro-$C_{1-20}$-alkyl group or a linear, branched or cyclic $C_{1-10}$-alkenyl group,
  R$^2$ is a linear or branched $C_{1-4}$-alkyl group, and
  n is 0 or 1 or 2, m is 0 or 1 and (n+m) is 1 or 2 or 3, or

  (II), wherein R$^4$ is a linear or branched $C_{1-8}$-alkyl group or a glycol ether unit of the formula: —[(CH$_2$)$_y$—O]$_z$—R$^5$ in which y is 2, 4, 6 or 8, z is 1, 2, 3 or 4 and R$^5$ is a linear or branched $C_{1-3}$-alkyl group.

Particularly preferred alkoxysilane products of the invention include tetramethoxysilane, tetraethoxysilane, tetrapropoxysilane, methylglycol orthosilicate, ethylglycol orthosilicate, methyltrimethoxysilane, methyltriethoxysilane, dimethyldimethoxysilane, dimethyldiethoxysilane, ethyltrimethoxysilane, ethyltriethoxysilane, 2-chloroethyltriethoxysilane, vinyltrimethoxysilane, vinyltriethoxysilane, vinylmethyldiethoxysilane, vinyltris(2-methyloxyethoxy)silane, phenyltrimethoxysilane, 2-phenylethyltrimethoxysilane, diphenyldimethoxysilane, propyltrimethoxysilane, propyltriethoxysilane, 3-chloropropyltrimethoxysilane, 3-chloropropyltriethoxysilane, propylmethyldimethoxysilane, propylmethyldiethoxysilane, 3-chloropropylmethyldimethoxysilane, 3-chloropropylmethyldiethoxysilane, isobutyltrimethoxysilane, isobutyltriethoxysilane, amyltrimethoxysilane, amyltriethoxysilane, octyltrimethoxysilane, octyltriethoxysilane, cyclohexyltrimethoxysilane, cyclohexylmethyldimethoxysilane, hexadecyltrimethoxysilane and hexadecyltriethoxysilane.

However, the process of the invention can also be used advantageously to prepare bis(trialkoxysilyl)alkanes, bis(methylalkoxysilyl)alkanes and bis(dimethylalkoxysilyl)alkanes, preferably the alkoxy groups being methoxy and ethoxy groups and the linear alkane groups having 1–16 carbon atoms.

Where, following the esterification, there are relatively large amounts of acidic chloride in the product mixture, for example, when more than 1% by weight of acidic chloride, based on the alkoxysilane, is present in the product mixture, it is possible if desired, in the case of a batchwise process, to cool the product mixture to a preferred temperature ranging from 10–60° C., preferably ranging from 20–50° C., to subject the product mixture to initial neutralization by adding metal alcoholate and then to remove the resultant salt by filtration.

It has been found that neutralization may, when conducted at a relatively high temperature, give rise to secondary reactions and so reduce the product yield. It has also been found that in some products obtained by initial neutralization of acidic chloride with a base and subsequent removal of resultant salt, it is possible after a short time to detect acidic chloride again.

In the process of the invention, prior to distillation, the product mixture obtained from the esterification is treated with the base preferably at a temperature in the range of 25 to <40° C., particularly preferably from 30–38° C.

The period for which the product mixture containing metal alcoholate is treated in the liquid phase prior to distillation is, in particular, up to 4 hours, preferably from 10–120 minutes and, particularly preferably from 15–90 minutes. Generally, distillation is conducted next in the process.

However, for the process of the invention, it is also possible and appropriate before beginning the distillation to subject the metal alcoholate-treated product mixture, for the purpose of gentle neutralization, in order to remove of any traces of acidic chloride, to after-treatment with an equivalent amount or preferably a slight stoichiometric excess of ammonia. Gaseous or liquid ammonia can be used for this purpose. Such an after-treatment is preferably conducted in the manner of a fine neutralization, particularly gentle to the product, with thorough mixing at a temperature ranging from 30 to <40° C.

In the process of the invention the product mixture obtained from the esterification is treated preferably for 10 minutes to 4 hours. This includes both the time for the treatment of the product mixture with metal alcoholate and, if appropriate, the time for the after-treatment with ammonia.

The above-described combination of an alcoholate/ammonia treatment in the context of the present process can be employed, for example, in connection with the preparation of 3-chloropropyltrimethoxysilane, 3-chloropropylmethyldimethoxysilane, 3-chloropropyltriethoxysilane or 3-chloropropylmethyldimethoxysilane.

For the distillation step, the product mixture from the esterification is generally transferred to the liquid phase of a distillation unit, with an equimolar amount or a stoichiometric excess of base, added in accordance, for example, with a continuous determination of the content of acidic chloride in the product mixture. The base can, for instance, be supplied even to the stream of the product mixture between esterification and the distillation unit. It is suitable to combine the product mixture and base with thorough mixing. Thorough mixing can be achieved, for example, by stirring, among other techniques.

In the process of the invention the metal alcoholate employed is an alkali metal or alkaline earth metal alcoholate, particularly preferably sodium, potassium or magnesium alcoholate. The alcoholates are suitably employed in the form of alcoholic solutions, with the alcoholate preferably corresponding to an alcohol that is employed.

In the process of the invention the distillation is generally conducted under reduced pressure, with the option of adapting the liquid phase temperature to the requirements of the respective alkoxysilane and with the pure product suitably being removed from the top of the column. One particular advantage, especially in the context of the economy of the process of the invention, is that the neutralization product of metal alcoholate, acidic chloride and, if appropriate, ammonia is preferably discharged together with the distillate residue from the distillation and it is possible to omit an additional step of filtration.

Products obtained by the process of the invention are generally notable for the following advantageous qualities:

high product purity (GC>99%);

acidic chloride content usually <5 ppm by weight, with acidic chloride contents of <1 ppm by weight being achievable;

water-clear products having a very low color number (usually <5 APHA);

excellent storage stability without subsequent precipitation of dissolved salts;

optimized and reproducible hydrolysis characteristics;

broad spectrum of use as a consequence of the minimal impurities.

Having now generally described the invention, a further understanding can be obtained by reference to certain specific examples which are provided herein for purpose of illustration only and are not intended to be limiting unless otherwise specified.

EXAMPLES

Example 1A

Comparative Example

Preparation of 3-chloropropyltrimethoxysilane (CPTMO) as described in EP 0 282 846 A2

A 212 kg (1 kmol) amount of 3-chloropropyltrichlorosilane (CPTCS) is placed in a batch-wise esterification reactor at a temperature of 50–60° C. and a total of 110 kg (3.4 kmol) of methanol is metered thereinto over a period of 5 hours. The methanol is added below the surface of the liquid by means of an immersed tube. After the addition of methanol is complete, the crude product is refluxed at about 80° C. for a further 2 hours. The HCl formed in the reaction is driven from the reaction mixture by means of a stream of dry $N_2$. Subsequently, the crude ester formed is diluted with about 200 kg of toluene, neutralized at 80° C. with sodium methoxide solution (about 20 mol. % excess, based on 1 mol. of hydrolyzable chlorine in the produce) and cooled to room temperature. Sodium chloride formed is removed by filtration and the filtrate is worked-up by distillation (vacuum distillation).

After separating the low boilers (methanol, toluene), about 161 kg (81%) of CPTMO having purity determined by gas-chromatographic of about 94% by weight of CPTMO and about 6% by weight of 3-methoxypropyltrimethoxysilane (MOPTMO) and a hydrolyzable chloride content of about 25 ppm are obtained. The distillation residue formed (about 40 kg, comprising siloxanes and oligomers) is discarded.

Example 1B

Comparative Example

Preparation of CPTMO as described in EP 0 532 872 B1

The crude CPTMO product prepared as described in Example 1A, but not neutralized and diluted with toluene, (hydrolyzable chloride content about 4.8% by weight) is, as described in EP 0 532 872 B1, treated with methanol and ammonia (about 10 mol. % excess, based on the hydrolyzable chloride content) for one hour at about 80° C. in a pressure autoclave. The cooled crude product is freed of precipitated ammonium chloride by filtration under pressure (Seitz filter) (residual hydrolyzable chloride content about 85 ppm) and purified by means of fractional distillation under reduced pressure. The distillation gives about 85% by weight of CPTMO having a gas-chromatographic purity of >0.5% by weight and a hydrolyzable chloride content of 46 ppm.

Example 1C

Preparation of CPTMO

A 212 kg (1 kmol) amount of 3-chloropropyltrichlorosilane (CPTCS) is placed in a batch-wise esterification reactor at a temperature of 50–60° C. and is reacted with a total of 110 kg (3.4 kmol) of methanol over a period of 5 hours. The methanol is metered in below the surface of the liquid by means of an immersed tube. During the course of the metered addition of methanol, the internal reactor temperature is kept by continual further heating at such a level that the crude ester mixture refluxes continually but the internal temperature does not exceed 110–115° C. To remove the HCl which is formed, the entire reaction is conducted under slightly reduced pressure (about 100 mbar) while at the same time removing unreacted methanol (HCl stripping alcohol) by distillation.

However, the stripping process is begun only when about 60% of the stoichiometric amount of methanol has been consumed. For stripping, a further 40 kg amount of methanol is additionally metered into the boiling reaction mixture, but the methanol immediately distills from the reactor again together with the HCl formed and can be reused in the next reaction batch.

After the metered addition of methanol is complete, the acidic reaction mixture is cooled to room temperature and the hydrolyzable chloride content is determined by titration with 0.1 N NaOH (residual chloride content from about 0.5–1.0 ml of 0.1 N NaOH). The neutralization can be conducted either directly in the esterification reactor or in the distillation pot. Usually, the crude product is transferred to the distillation pot and is there admixed at temperatures ranging from 30–40° C. with a small stoichiometric excess of sodium methoxide solution (30% strength in methanol) or magnesium methoxide solution (saturated solution in methanol) and neutralized while stirring for 60 minutes. The amount of metal alkoxide solution required for fine neutralization is metered in until the crude product has an alkalinity which corresponds to a consumption of from 1–2 ml of 0.1 N HCl in the titration. It is likewise possible to use ammonia as a neutralizing agent, in which case the end of the neutralization is indicated by a consumption of about 5 ml of 0.1 N HCl during the titration. The choice of neutralizing agent is determined by the desired quality criteria for the pure CPTMO product. After the neutralization is complete, the crude product is purified by means of fractional distillation under reduced pressure and the salt which is formed is discharged with the distillation residue (without further filtration).

The process described above gives about 95% by weight of CPTMO having a GC purity of >99%, a MOPTMO content of <0.3% and a hydrolyzable chloride content of <5 ppm (use of $NaOCH_3$ solution or $NaOCH_3/NH_3$ combination as neutralizing agent). When using magnesium methoxide solution, 95% by weight having a GC purity of >99.5%, a MOPTMO content of <0.1% and a hydrolyzable chloride content of <1 ppm are obtained.

Example 2A

Comparative Example

Preparation of vinyltriethoxysilane (VTEO) as described in EP 0 282 846 A2

Using the procedure of Comparative Example 1A, a 161.5 kg (1 kmol) amount of vinyltrichlorosilane (VEC) is reacted with a total of 152 kg (3.3 kmol) of ethanol and neutralized with sodium methoxide solution (21% strength in ethanol) in a 20 mol. % excess (based on 1 mol. of hydrolyzable chloride in the crude product) and, after filtration, worked-up by distillation.

This gives about 127 kg (86%) of VTEO having a GC purity of 97.5%, a tetraethoxysilane content of 2500 ppm, a hydrolyzable chloride content of 17 ppm and a color number of 10 APHA.

Example 2B

Comparative Example
Preparation of VTEO as described in EP 0 532 872 B1

Using the procedure of Comparative Example 1 B, VTEO crude product prepared as described in Comparative Example 2A but not neutralized (hydrolyzable chloride content about 2.1% by weight) is treated with ethanol and ammonia (about 10 mol. % excess of $NH_3$, based on the hydrolyzable chloride content) for one hour at 100° C. in a pressure autoclave. Filtration and distillation gives about 88.5% by weight of VTEO having a GC purity of 97.8%, a tetramethoxysi lane content of <800 ppm, a hydrolyzable chloride content of 64 ppm and a color number of 5 APHA.

Example 2C

Preparation of VTEO

Using the procedure of Example 1C, a 161.5 kg (1.0 kmol) amount of VTC is reacted with a total of 152 kg (3.3 kmol) of ethanol using the stripping process and, without prior filtration, neutralized in the distillation pot with sodium methoxide solution (21% strength in ethanol) or with magnesium ethoxide solution (saturated solution in ethanol). The end point of the neutralization is achieved at a crude product alkalinity: which corresponds to a consumption of from 1–2 ml of 0.1 N HCl. Purification by distillation gives about 92% by weight of VTEO having a GC purity of >99%, a tetraethoxysilane content of <800 ppm, a hydrolyzable chloride content of <1 ppm and a color number of <5 APHA. When using magnesium ethoxide solution as neutralizing agent, 94% by weight of VTEO having a GC purity of >99%, a tetraethoxysilane content of <300 ppm, a color number of <5 APHA and a hydrolyzable chloride content of <1 ppm are obtained.

Example 2D

Continuous preparation of VTEO

In a continuous esterification plant comprising reactor column and light ends column, about 100 kg/h of vinyltrichlorosilane and from 80–90 kg/h of ethanol are metered simultaneously into the reactor column at about 60° C. and atmospheric pressure and are reacted there. The hydrogen chloride which is formed is discharged from the top of the column. The strongly acidic, crude silane ester product (acidity about 5000 ppm) leaves the reactor column at the bottom and is metered by means of a pump into a second esterification column (light ends column). In the light ends column, the not yet completely reacted chlorosilanes (about 5000 ppm) are after-esterified by addition of a small amount of added ethanol (about 10–20 kg) and HCl still dissolved in the crude product is driven from the top of the light ends column at the boiling point of the crude product (about 80–90° C.). Excess ethanol is likewise discharged at the top of the light ends column and is fed back into the reactor column. The desorbed crude product leaves the light ends column at the bottom and, after cooling in a plurality of heat exchangers, is pumped into the crude product container. The crude ester prepared in this way has a high GC purity and a low residual acidity (acidity at most 200 ppm, VTEO content >98%, siloxane content <1%, ethanol content <1%).

The crude VTEO product can be purified by means of either continuous or batchwise distillation with addition of sodium ethoxide or magnesium ethoxide solution (as neutralizing agent, neutralization end point at consumption of 1.5 ml of 0.1 N HCl). The sodium or magnesium chloride which is formed is discharged with the distillation bottoms (cf. Example 1C).

The stated process gives a yield of about 96% by weight of VEEO having a GC purity of >99.3%, a tetraethoxysilane content of <200 ppm, a color number of <5 APHA and a hydrolyzable chloride content of <1 ppm.

Example 3A

Comparative Example
Preparation of hexedecyltrimethoxysilane as described in EP 0 282 846 A2

Using the procedure of Comparative Example 1A, a 360 kg (1 kmol) amount of hexadecyltrichlorosilane is reacted with a total of 110 kg (3.4 kmol) of methanol and neutralized with sodium methoxide solution (30% strength in methanol) in a 20 mol. % excess (based on 1 mol. of hydrolyzable chloride in the crude product) and, after filtration, worked-up by distillation. This procedure gives about 280 kg (81%) of hexadecyltrimethoxysilane having a GC purity of 98.5% (isomer mixture), a color number of 10 APHA and a hydrolyzable chloride content of 12 ppm.

Example 3B

Comparative Example
Preparation of hexadecyltrimethoxysilane as described in EP 0 532 872 B1

Using the procedure of Comparative Example 1 B, a crude product prepared as described in Comparative Example 3A, but not neutralized (hydrolyzable chloride content about 1.8% by weight), is treated with methanol and ammonia (about 10 mol. % excess of $NH_3$, based on the hydrolyzable chloride content) for one hour at about 100° C. in a pressure autoclave. After filtration and distillation, about 86% of hexadecyltrimethoxysilane having a GC purity of 98.4% (isomer mixture), a color number of <10 APHA and a hydrolyzable chloride content of 47 ppm is obtained.

Example 3C

Preparation of hexadecyltrimethoxysilane

Using the procedure of Example 1C, a 360 kg (1 kmol) amount of hexadecyltrichlorosilane is reacted with a total of 100 kg (1 kmol) of methanol using the stripping process and a metered addition time of 12 hours and, without prior filtration, neutralized in the distillation pot with sodium methoxide solution (30% strength in methanol) or with magnesium methoxide solution (saturated solution in methanol). The end point of the neutralization is achieved at a crude product alkalinity which corresponds to a consumption of 2 ml of 0.1 NHCl.

Purification by vacuum distillation gives about 95.3% by weight of hexadecyltrimethoxysilane having a GC purity of >99% (isomer mixture), a color number of <5 APHA and a hydrolyzable chloride content of <2 ppm. When using magnesium methoxide solution, 96% by weight of hexadecyltrimethoxysilane in otherwise the same final product quality is obtained.

Example 4A

Comparative Example
Preparation of tetra(2-methoxyethoxy)silane (CM) as described in EP0282 846 A2

Using the procedure of Comparative Example 1A, a 170 kg (1 kmol) amount of tetrachlorosilane is reacted with a total of 335 kg (4 kmol) of methylglycol and is neutralized with sodium methoxide solution (30% strength in methanol) in a 20 mol. % excess (based on 1 mol. of hydrolyzable chloride in the crude product) and worked-up by filtration and subsequent distillation.

This procedure gives about 284 kg (86.5%) of tetra(2-methoxyethoxy)silane having a GC purity of 97.3%, a 2-chloroethoxytris(2-methoxyethoxy)silane content of 1.9%, a color number of 15 APHA and a hydrolyzable chloride content of 27 ppm.

Example 4B

Comparative Example
Preparation of tetra(2-methoxyethoxy)silane as described in EP 0 532 872 B1

Using the procedure of Comparative Example 1 B, a crude CM product prepared as described in Comparative Example 4A, but not neutralized (hydrolyzable chloride content about 2.1% by weight), is treated with methylglycol and ammonia (about 10 mol. % excess of $NH_3$, based on the hydrolyzable chloride content) for one hour at about 80° C. in a pressure autoclave. After filtration and distillation, about 88% by weight of tetra(2-methoxyethoxy)silane having a GC purity of 97.8%, a 2-chloroethoxytris(2-methoxyethoxy) silane content of 0.85%, a color number of 10 APHA and a hydrolyzable chloride content of 61 ppm is obtained.

Example 4C
Preparation of tetra(2-methoxyethoxy)silane (CM)

Using the procedure of Example 1C, a 170 kg (1 kmol) amount of tetrachlorosilane is reacted with a total of 335 kg (4.4 kmol) of methylglycol using the stripping process and, without prior filtration, neutralized in the distillation pot with sodium methoxide solution (30% strength in methanol) or with magnesium methoxide solution (saturated solution in methanol). The neutralization end point is reached at a crude product alkalinity corresponding to a consumption of from 1–2 ml of 0.1 N HCl.

After work-up by distillation under reduced pressure, about 92% by weight of tetra(2-methoxyethoxy)silane having a GC purity of >99.5%, a color number of 5 APHA, a 2-chloroethoxytris(2-methoxyethoxy)silane content of <0.4% and a hydrolyzable chloride content of <5 ppm are obtained. When using magnesium methoxide solution, about 93.5%, by weight of pure product (CM) having a GC purity of >99.7%, a color number of <5 APHA, a 2-chloroethoxytris(2-methoxyethoxy)silane content of <0.4% and a hydrolyzable chloride content of <5 ppm is obtained.

Example 4D
Continuous preparation of tetra(2-methoxyethoxy)silane (CM)

In a continuous esterification plant comprising light ends column and reactor column, about 60 kg/h of tetrachlorosilane and from 120–130 kg/h of methylglycol are metered simultaneously into the reactor column at about 55° C. and atmospheric pressure and are reacted. The hydrogen chloride which is formed is removed at the top of the column, and the strongly acidic, crude silane ester product leaves the reactor column at the bottom and is metered by means of a suitable pump into a second esterification column (light ends column). In the light ends column, the not yet completely reacted chlorosilane (about 500 ppm) is after-esterified by introduction of a further amount of methylglycol (about 20 kg/h) and HCl still dissolved in the crude product is driven from the top of the column at the boiling point of the crude product (from 120–145° C.). Excess methylglycol is likewise discharged at the top of the light ends column and is fed back into the reactor column.

The desorbed crude product leaves the light ends column at the bottom and, after cooling in a plurality of heat exchangers, is pumped into a crude product container. The crude ester prepared in this way has a high purity and a low residual acidity (acidity at most 50 ppm, siloxane content <3%, methyl glycol content <5%, CM content >92%).

The crude silane ester product can be purified by means of either continuous or batchwise distillation with addition of sodium methoxide or magnesium methoxide solution (as neutralizing agent, neutralization end point at consumption of 2 ml of 0.1 N HCl). The sodium or magnesium chloride which is formed is discharged with the distillation bottoms (cf. Example 1 C).

This gives a yield of from 93–95% by weight of tetra(2-methoxyethoxy)silane having a GC purity of >99.5%, a color number of 5APHA, a 2-chloroethoxytris(2-methoxyethoxy)silane content of <01% and a hydrolyzable chloride content of <5 ppm The disclosure of the German priority patent Applications Number 198 51 148.5 filed Nov. 6, 1998 and Number 199 41 590.0 filed Aug. 31, 1999 are hereby incorporated by reference into the present application.

Obviously, numerous modifications and variations of the present invention are possible in light of the above teachings. It is therefore to be understood that within the scope of the appended claims, the invention may be practiced otherwise than as specifically described herein.

What is claimed as new and is intended to be secured by Letter Patent is:

1. A process for preparing alkoxysilanes, comprising:
   (i) reacting a chlorosilane with an alcohol in a water-free and solvent free phase with removal of the liberated hydrogen chloride;
   (ii) transferring the resultant product mixture into a liquid phase to be distilled and adding a metal alcoholate to the product mixture in the liquid at a temperature in the range from 10–60° C., and thoroughly mixing the neutralized product mixture, said alcoholate being employed in an equimolar amount or in a stoichiometric excess based on the amount of acidic chloride, and
   (iii) purifying the treated product mixture by distillation under reduced pressure, thereby preparing alkoxysilanes which are low in acidic chloride or essentially free of acidic chloride.

2. The process as claimed in claim 1, wherein, during the reaction of chlorosilane and alcohol, alcohol in liquid form is added continuously to the medium in order to remove the hydrogen chloride which forms in the reaction, and an excess fraction of the alcohol employed is removed from the top of the reactor.

3. The process as claimed in claim 1, wherein the addition of the metal alcoholate to the product mixture in the liquid phase of the distillation and the subsequent treatment are conducted with thorough mixing at a temperature of from 25 to <40 ° C.

4. The process as claimed in claim 1, wherein the product mixture is treated for up to 4 hours in the liquid phase of the distillation unit prior to beginning the distillation and then the distillation is subsequently conducted.

5. The process as claimed in claim 1, wherein, prior to the beginning of the distillation the metal alcoholate-treated product mixture is subjected, for the purpose of neutralizing any traces of acidic chloride, to aftertreatment with an equivalent amount or with a stoichiometric excess of ammonia.

6. The process as claimed in claim 1, wherein the neutralization products of metal alcoholate and acidic chloride are discharged together with the distillate residue from the distillation.

7. The process as claimed in claim 6, wherein the neutralization products of metal alcoholate, acidic chloride and ammonia are discharged together with the distillate residue from the distillation.

8. The process as claimed in claim 1, wherein the alcohol employed is methanol, ethanol, isopropanol, n-propanol, methylglycol or ethylglycol.

9. The process as claimed in claim 1, wherein the metal alcoholate is employed in the form of an alcoholic solution.

10. The process as claimed in claim 1, wherein the alcoholate ion of the metal alcoholate corresponds to the alcohol that is used.

11. The process as claimed in claim 1, wherein the metal alcoholate employed is an alkali metal alcoholate or an alkaline earth metal alcoholate.

12. The process as claimed in claim 11, wherein the metal alcoholate employed is sodium alcoholate or potassium alcoholate or magnesium alcoholate.

13. The process as claimed in claim 1, which is conducted under an inert gas.

14. The process as claimed in claim 1, which is conducted as a continuous process.

15. The process as claimed in claim 1, wherein the alkoxysilane has the formula I or II:

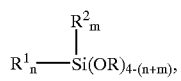
(I)

wherein
R is a linear or branched $C_{1-4}$-alkyl or a glycol ether unit of the formula: $—[(CH_2)_y—O]_z—R^3$ $R^3$ in which y is 2, 4, 6 or 8, z is 1, 2, 3 or 4 and $R^3$ is a linear or branched $C_{1-8}$-alkyl group, $R^1$ is a linear, branched or cyclic $C_{1-20}$-alkyl group, a linear, branched or cyclic chloro-$C_{1-20}$-alkyl group or a linear, branched or cyclic $C_{1-10}$-alkenyl group, $R^2$ is a linear or branched $C_{1-4}$-alkyl group, and n is 0 or 1 or 2, m is 0 or 1 and (n+m) is 1 or 2 or 3, or $$Si(OR^4)_4 \qquad (II),$$

wherein $R^4$ is a linear or branched $C_{1-8}$-alkyl group or a glycol ether unit of the formula: $—[(CH_2)_y—O]_z—R^5$ in which y is 2, 4, 6 or 8, z is 1, 2, 3 or 4 and $R^5$ is a linear or branched $C_{1-8}$-alkyl group.

16. The process as claimed in claim 1, wherein the chlorosilane is 2-chloroethyltrichlorosilane, vinylmethyldichlorosilane, allyltrichlorosilane, 3-allyloxypropyltrichlorosilane, butyltrichlorosilane, pentyltrichlorosilane, cyclopentyltrichlorosilane, cyclopentylmethyldichlorosilane, phenyltrichlorosilane, cyclohexyltrichlorosilane, octyl methyldichlorosilane, dodecyltrichlorosilane, benzyltrichlorosilane, benzylmethyldichlorosilane, 2-phenylethyltrichlorosilane or diphenyldichlorosilane, tetrachlorosilane, methyltrichlorosilane, dimethyldichlorosilane, trimethylchlorosilane, ethyltrichlorosilane, 3-chloropropyltrichlorosilane, 3-chloropropylmethyldichlorosilane, cyclohexylmethyldichlorosilane, vinyltrichlorosilane, propyltrichlorosilane, propylmethyldichlorosilane, isobutyltrichlorosilane, amyltrichlorosilane, octyltrichlorosilane, hexadecyltrichlorosilane or hexadecyhnethyldichlorosilane.

17. The process as claimed in claim 1, wherein the alcohol reactant is a $C_{1-20}$-monohydric primary alcohol, a cyclic alcohol, an aromatic alcohol, a monoether of a polyalkylene glycol, a di-, tri- or tetramethylene glycol monomethyl, monoethyl, monopropyl or monobutyl ether or a dihydric aliphatic alcohol.

18. The process as claimed in claim 3, wherein the temperature of said thorough mixing ranges from 30–38° C.

* * * * *

UNITED STATES PATENT AND TRADEMARK OFFICE
CERTIFICATE OF CORRECTION

PATENT NO. : 6,242,628 B1  
DATED : June 5, 2001  
INVENTOR(S) : Kropfgans et al.

Page 1 of 1

It is certified that error appears in the above-identified patent and that said Letters Patent is hereby corrected as shown below:

<u>Title page,</u>
Item [30], the Foreign Application Priority Data should read, -- [30]          Foreign Application Priority Data

Nov. 6, 1998 (DE).................................................................... 198 51 148  
Sep. 1, 1999 (DE).................................................................... 199 41 590 --

Signed and Sealed this

Fifth Day of February, 2002

Attest:

JAMES E. ROGAN  
*Attesting Officer*     *Director of the United States Patent and Trademark Office*